United States Patent
Artús Surroca et al.

(10) Patent No.: US 7,291,746 B2
(45) Date of Patent: Nov. 6, 2007

(54) PROCESS FOR OBTAINING AN ANTIEPILEPTIC AGENT

(75) Inventors: Juan José Artús Surroca, Vilanova i la Geltrú (ES); Llorenç Rafecas Jané, Llorenç del Penedès (ES); Lourdes Garriga Sanahuja, Banyeres del Penedès (ES); Miquel A. Pericas Brondo, Esplugues del Llobregat (ES); Lluís Solà Carandell, La Garriga (ES)

(73) Assignee: Esteve Quimica, S.A., Barcelona (ES)

( * ) Notice: Subject to any disclaimer, the term of this patent is extended or adjusted under 35 U.S.C. 154(b) by 130 days.

(21) Appl. No.: 10/544,967

(22) PCT Filed: Feb. 6, 2004

(86) PCT No.: PCT/ES2004/000050

§ 371 (c)(1), (2), (4) Date: Aug. 8, 2005

(87) PCT Pub. No.: WO2004/076416

PCT Pub. Date: Sep. 10, 2004

(65) Prior Publication Data

US 2006/0142376 A1 Jun. 29, 2006

(30) Foreign Application Priority Data

Feb. 28, 2003 (ES) ................. 200300482

(51) Int. Cl.
- C07D 207/26 (2006.01)
- A61K 31/4015 (2006.01)

(52) U.S. Cl. ............... 548/543; 548/518; 514/422; 514/424

(58) Field of Classification Search ............... 544/141, 544/372; 546/208; 548/524, 518, 543; 514/422, 514/424

See application file for complete search history.

(56) References Cited

U.S. PATENT DOCUMENTS

| 6,107,492 A * | 8/2000 | Futagawa et al. ............ 548/543 |
| 6,124,473 A * | 9/2000 | Cavoy et al. ................ 548/550 |

* cited by examiner

*Primary Examiner*—Joseph K. McKane
*Assistant Examiner*—Janet L. Coppins

(57) ABSTRACT

A process for obtaining the pharmaceutical active ingredient, levetiracetam, by means of deaminomethylation of a sufficiently pure enantiomer intermediate (S)-(II), or by means of deaminomethylation of an addition salt thereof with an acid, wherein $R_1$ and $R_2$ are either the same or different $(C_1-C_6)$-alkyl radicals, or else $R_1$ and $R_2$ together with the nitrogen atom to which they are bonded form a radical selected from the group consisting of 1-pyrrolidinyl, 1-piperidinyl, 1-morpholinyl, 1-piperazinyl and 1-[4-$(C_1$-$C_4)$-alkylpiperazinyl]. The invention also comprises preparing the sufficiently pure enantiomer intermediate (S)-(II) by treating the corresponding chemically new racemic intermediate (II) with an amine resolving agent, followed by selective crystallisation of a diastereoisomeric salt thereof. It is useful for obtaining levetiracetam on an industrial scale and involves neither hydrogenation nor chromatography

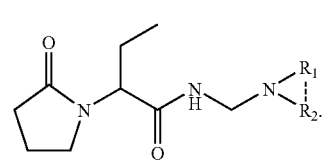
(II)

27 Claims, No Drawings

PROCESS FOR OBTAINING AN ANTIEPILEPTIC AGENT

The present invention refers to obtaining the antiepileptic active ingredient known as levetiracetam, of formula (S)-(I), as well as intermediate compounds for said obtainment.

PRIOR STATE OF THE ART

Levetiracetam is the International Non-proprietary Name (INN) of a pharmaceutical active ingredient called (αS)-α-ethyl-2-oxo-1-pyrrolidineacetamide and having the formula:

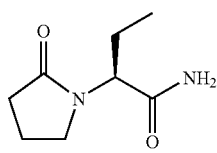

(S)-(I)

It is the (S)-enantiomer of the racemic product etiracetam of formula (I), known since the 1970s.

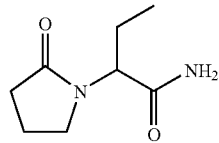

(I)

Patent application EP 162,036-A1 discloses levetiracetam for the first time and it is indicated that it has particular therapeutic properties distinguishing it from the racemic form, given that it is provided with an activity that is ten times higher with regard to protection against hypoxia (absence of a suitable amount of oxygen in tissues) and four times higher with regard to protection against cerebral ischemia.

Several processes for obtaining levetiracetam have been disclosed in the art. Patent application EP 162,036-A1 discloses obtaining levetiracetam by reacting (S)-α-ethyl-2-oxo-1-pyrrolidineacetic acid with an alkyl haloformate and subsequently with ammonia, as summarized in the following scheme:

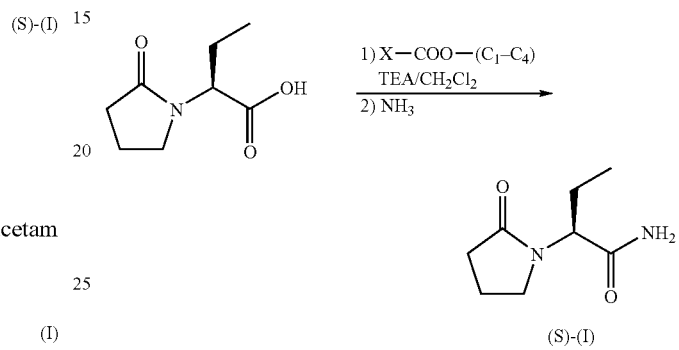

The same document discloses obtaining levetiracetam by reacting (S)-2-amino-butanamide with an alkyl 4-halobutyrate or with a 4-halobutyryl halide, and subsequent cyclization of alkyl (S)-4-[[1-(aminocarbonyl)propyl]amino]butyrate or of (S)-N-[1-(aminocarbonyl)propyl]-4-halobutanamide thus obtained, as summarized in the attached scheme:

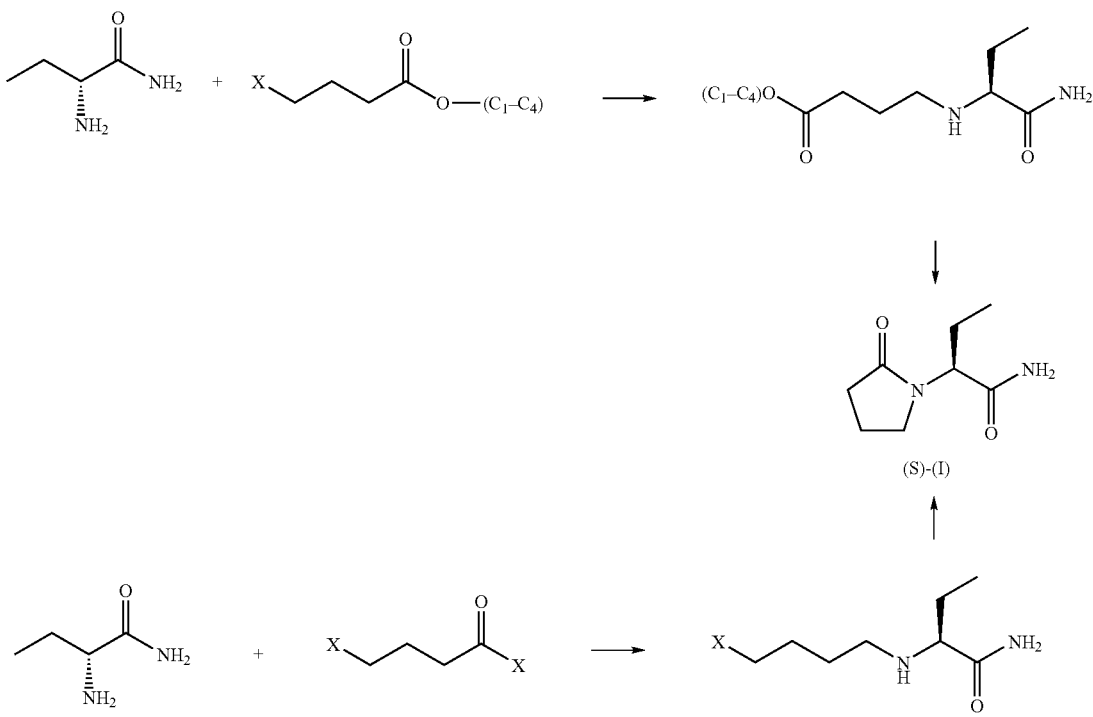

The two previous processes have the drawback of operating at temperatures between −10° C. and −60° C. and the drawback of using intermediates for cyclization that are not readily obtained.

Patent application GB 2,225,322-A1 discloses a process for obtaining levetiracetam by hydrogenolysis of (S)-α-[2-(methylthio)ethyl]-(2-oxo-1-pyrrolidine)acetamide by means of a desulfurizing reagent such as Raney nickel or $NaBH_4 \cdot NiCl_2 \cdot 6H_2O$, according to the following scheme:

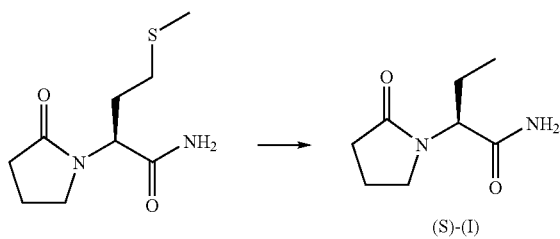

(S)-(I)

A drawback of this industrial-scale process is that it requires special equipment and special precautions for handling the products.

Other processes are known (for example U.S. Pat. Nos. 6,107,492 and 6,124,473) in which levetiracetam is obtained by means of optical resolution of racemic etiracetam of formula (I). In U.S. Pat. No. 6,107,492 resolution is performed by means of preparative high performance liquid chromatography or by means of a continuous simulated fluid bed chromatographic system with a chiral stationary phase. U.S. Pat. No. 6,124,473 discloses a continuous simulated fluid bed chromatographic system consisting of at least three chiral stationary phase columns. These industrial-scale resolution processes are affected by drawbacks related to using chromatography.

Finally, patent applications WO 01/64,637-A1 and WO 02/26,705-A2 disclose processes for preparing levetiracetam by asymmetric hydrogenation of intermediates with a double bond, the hydrogenation of which gives the levetiracetam ethyl group, according to the following scheme:

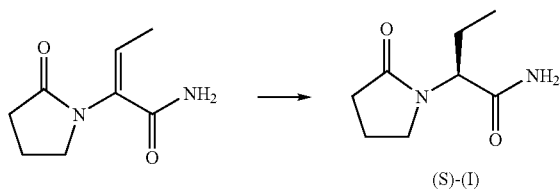

(S)-(I)

The industrial-scale difficulties and hazard of hydrogenation can be mentioned in relation to these processes.

It is therefore interesting to have alternative processes for preparing levetiracetam, particularly if they are easy to industrialize and do not involve hydrogenation or chromatographic separation.

SUMMARY OF THE INVENTION

According to one aspect of the present invention, a new process for obtaining levetiracetam (S)-(I) is provided, comprising subjecting a sufficiently pure enantiomer intermediate (S)-(II) or an addition salt thereof with an acid to a deaminomethylation reaction,

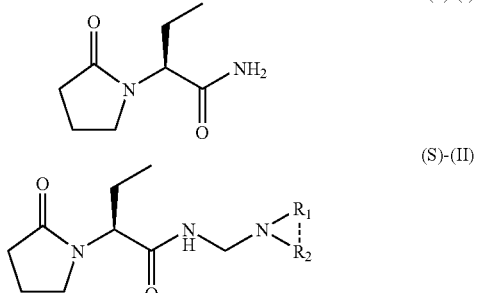

wherein $R_1$ and $R_2$ are the same or different $(C_1-C_6)$-alkyl radicals, or $R_1$ and $R_2$ together with the nitrogen atom to which they are bonded form a radical selected from the group consisting of 1-pyrrolidinyl, 1-piperidinyl, 1-morpholinyl, 1-piperazinyl and 1-[4-($C_1$-$C_4$)-alkylpiperazinyl].

In a preferred embodiment, the sufficiently pure enantiomer intermediates (S)-(II) are those in which $R_1$ and $R_2$ are both ethyl, or $R_1$ and $R_2$ together with the nitrogen atom to which they are bonded, form a radical selected from the group consisting of 1-pyrrolidinyl and 1-piperidinyl. Even more preferable is the embodiment in which $R_1$ and $R_2$ are both ethyl.

Sufficiently pure enantiomer intermediate (S)-(II) or an addition salt thereof with an acid is understood as that which has enough enantiomeric excess for industrial-scale preparation, which depends on each specific case as the person skilled in the art will find when the invention is exploited. From a purely theoretical point of view it would even be enough for it to have an enantiomeric excess simply higher than 50%. However, for industrial-scale preparation it must preferably be understood that it is sufficiently pure in this sense when it has a purity, that is, an enantiomeric excess (e.e.), exceeding 70%. It is particularly advantageous for the enantiomeric excess (e.e.) to be greater than or equal to 80% and very preferably greater than or equal to 90%.

In a particular embodiment, deaminomethylation is carried out on the sufficiently pure enantiomer intermediate (S)-(II), previously obtained by base treatment of said addition salt with an amine resolving agent acid.

Preferably, deaminomethylation is carried out on an addition salt of the sufficiently pure enantiomer intermediate (S)-(II) with an amine resolving agent acid. Amine resolving agent acid is understood as any optically active acid of those commonly used for resolving amines by diastereoisomeric salt crystallisation, (cfr. J. Jacques et al., "Enantiomers, Racemates, and Resolutions", Wiley, 1981; A. N. Collins et al., "Chirality in Industry", John Wiley & Sons, 1992). In the present invention, the preferred acids are those selected from one of the enantiomers of tartaric acid, 1-camphor-10-sulfonic acid, malic acid, dibenzoyltartaric acid, mandelic acid, α-methoxyphenylacetic acid, α-methoxy-α-trifluoromethylphenylacetic acid, pyroglutamic acid, ditoluyltartaric acid or 3-bromocamphor-10-sulfonic acid. Even more preferably deaminomethylation is carried out on an addition salt of the sufficiently pure enantiomer intermediate (S)-(II) with L-(+)-tartaric acid.

Deaminomethylation can be carried out by treatment with an acid. The acid is preferably an acid from the group consisting of p-toluenesulfonic acid, methanesulfonic acid, benzenesulfonic acid and hydrochloric acid; hydrochloric acid being especially preferable. Alternatively, the reaction can be carried out by treatment with a base, where this base is preferably ammonia, pyrrolidine, piperidine, 1,2-trans-diaminocyclohexane, diisopropylamine, butylamine, potassium hydroxide and sodium hydroxide; butylamine being particularly preferable. It can also be carried out with the same bases in the presence of a minor amount of its hydrochloride. The reaction is preferably carried out in water or in an organic solvent/water mixture, being able to use as organic solvents, for example, ($C_1$-$C_5$) aliphatic monoalcohols, ($C_6$-$C_8$) hydrocarbons, ($C_3$-$C_9$) aliphatic esters, ($C_1$-$C_3$) aliphatic chlorides and mixtures of any of them, at a temperature comprised between 0° C. and the reflux temperature of the solvent system used.

Another aspect of the invention refers to a process for obtaining the sufficiently pure enantiomer intermediate (S)-(II) addition salt with an amine resolving agent acid that can generally be prepared by treating the corresponding racemic intermediate (II) with one of these acids, followed by one or several selective crystallisations of this diastereoisomeric salt in a suitable solvent system, where said salt is insoluble at a cold temperature, cold temperature being understood as not only room temperature but also temperatures below room temperature which can readily be reached on an industrial scale.

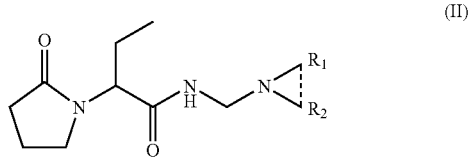

($C_1$-$C_5$) aliphatic monoalcohols, mixtures of ($C_1$-$C_5$) aliphatic monoalcohols with ($C_6$-$C_8$) aliphatic or aromatic hydrocarbons and mixtures of ($C_1$-$C_5$) aliphatic monoalcohols with ($C_3$-$C_7$) aliphatic ketones can be used as a solvent system. In a preferred embodiment, the solvent system is selected from the group consisting of methanol, ethanol, methanol/heptane mixtures, methanol/methyl isobutyl ketone mixtures, methanol/methyl ethyl ketone mixtures, ethanol/methyl isobutyl ketone mixtures, ethanol/methyl ethyl ketone mixtures and methanol/acetone mixtures. This reaction for obtaining the salt is carried out by means of well-known techniques, comprising reacting the racemic intermediate (II) with the amine resolving agent acid and, when required, seeding with a sample of the addition salt to be obtained, finally separating the crystallised product by means of filtering. The suitable conditions will be chosen by the person skilled in the art in each case according to parameters such as product concentration, type of solvent and the like, parameters that can be readily determined by means of routine tests.

The racemic intermediate (II) is obtained by reacting etiracetam (I) with formaldehyde, both free formaldehyde and in paraformaldehyde form, and a free amine of formula $HNR_1R_2$ or as a hydrochloride, wherein $R_1$ and $R_2$ have the previously defined meaning, according to the following scheme:

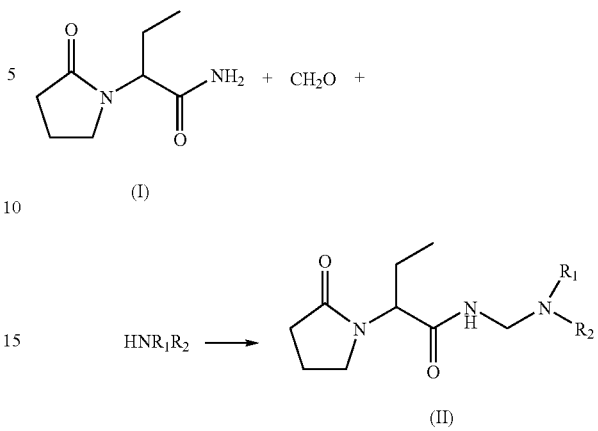

The etiracetam used as a starting material can be obtained by the process disclosed in British patent GB No 1,309,692.

A third aspect of the present invention refers to the new intermediate compounds of formula (II), their stereoisomers, mixtures thereof, solvates and addition salts of any of the foregoing, as well as solvates of said addition salts and hydrates of said addition salts, wherein $R_1$ and $R_2$ are either the same or different ($C_1$-$C_6$-alkyl radicals, or else $R_1$ and $R_2$, together with the nitrogen atom to which they are bonded, form a radical selected from the group consisting of 1-pyrrolidinyl, 1-piperidinyl, 1-morpholinyl, 1-piperazinyl and 1-[4-($C_1$-$C_4$)-alkylpiperazinyl]. The most preferred among them are those in which $R_1$ and $R_2$ are either both ethyl, or else $R_1$ and $R_2$ together with the nitrogen atom to which they are bonded, form a radical selected from the group consisting of 1-pyrrolidinyl and 1-piperidinyl. The intermediate compound (II) in which $R_1$ and $R_2$ are both ethyl is particularly preferred.

Preferable among the addition salts of intermediate (II), or its stereoisomers, or of the mixtures thereof, are the previously mentioned salts with amine resolving agent acids. Particularly preferable among them are those salts in which the amine resolving agent acid is L-(+)-tartaric acid, such as (S)-N-[(1,1-diethylamino)methyl]-α-ethyl-2-oxo-1-pyrrolidineacetamide L-(+)-tartrate, (S)-N-[(1-pyrrolidinyl)methyl]-α-ethyl-2-oxo-1-pyrrolidineacetamide L-(+)-tartrate or (S)-N-[(1-piperidinyl)methyl]-α-ethyl-2-oxo-1-pyrrolidineacetamide L-(+)-tartrate, as well as hydrates and solvates of all the previous salts.

In comparison with processes for preparing levetiracetam known in the art, the process of the present invention provides a simple and readily industrialised alternative for obtaining enantiomerically pure levetiracetam from a new sufficiently pure enantiomer intermediate (S)-(II) or from the addition salts thereof with amine resolving agent acids. Intermediate (S)-(II) is in turn readily obtained from racemic etiracetam with a good yield and by means of relatively economical conversions. The solvents used are common, inexpensive and little toxic, and L-(+)-tartaric acid is a natural, inexpensive and non-toxic acid. Furthermore, the opposite (R)-enantiomer absolute configuration of intermediate (S)-(II) or its addition salts with amine resolving acids, unsuitable for preparing levetiracetam, is easy to racemize in a manner equal to that shown in example 11 for the (S)-enantiomer. This allows recycling in the levetiracetam production process, preventing the loss of starting material.

The invention is illustrated below by means of several detailed examples, which must not be considered to be limitative of the scope of protection. Based on the information provided and general common knowledge, how to carry out the invention in its entire scope will be evident for the person skilled in the art. The word "comprise" and variants thereof are used in this description and claims in the sense that does not mean to exclude other elements, components or steps.

EXAMPLES

Example 1

Preparation of N-[(1-piperidinyl)methyl]-α-ethyl-2-oxo-1-pyrrolidineacetamide 58.6 ml of a 35% w/w solution of formaldehyde in $H_2O$ with 10% methanol were added to a dispersion of 50 g of etiracetam in 250 ml of ethanol in 15 minutes and at room temperature. 58 ml of piperidine were added to the resulting solution in 45 minutes and was maintained at 50° C. for 24 hours. The solvent was evaporated under reduced pressure, and after adding 233 ml of xylene, the solvent was evaporated again, an operation that was repeated another time, obtaining 89.8 g of a semi-solid, the crystallisation of which from 54 ml of heptane allowed obtaining 65.5 g of the compound indicated in the example title, characterised by the following analytical data: mp: 92° C.; $^1$H-NMR: (400 MHz, $CDCl_3$, ppm): 0.91 (t, 3H), 1.35-1.45 (m, 2H), 1.5-1.6 (m, 4H), 1.65-1.75 (m, 1H), 1.90-2.10 (m, 3H), 2.35-2.50 (m, 6H), 3.40-3.50 (m, 2H), 4.05-4.15 (m, 2H), 4.40-4.50 (m, 1H), 6.8 (bs, 1H); $^{13}$C-NMR (400 MHz, $CDCl_3$, ppm): 10.4 ($CH_3$), 18.1 ($CH_2$), 21.1 ($CH_2$), 23.9 ($CH_2$), 25.7 (2×$CH_2$), 31.0 ($CH_2$), 43.8 ($CH_2$), 50.9 (2×$CH_2$), 56.6 (CH); 61.6 ($CH_2$), 170.5 (C), 175.8 (C); IR (film, KBr, $cm^{-1}$): 3309, 2935, 1668, 1539, 1435, 1287, 1113, 861.

Example 2

Preparation of N-[(1-pyrrolidinyl)methyl]-α-ethyl-2-oxo-1-pyrrolidineacetamide 58.6 ml of a 35% w/w solution of formaldehyde in $H_2O$ with 10% methanol were added to a dispersion of 50 g of etiracetam in 250 ml of ethanol at 15° C. and in 20 minutes. Then 48.7 ml of pyrrolidine were added in 50 minutes. This was heated at 50° C. and maintained for 24 hours. Then the solvent was evaporated under reduced pressure, and after adding 233 ml of xylene, the solvent was evaporated again, an operation that was repeated another time, obtaining 81.6 g of the compound indicated in the example title in oil form, the recrystallisation of which from 49 ml of xylene allowed obtaining 42.3 g of the compound indicated in the example title, characterised by the following analytical data: mp: 75° C.; $^1$H-NMR (400 MHz, $CDCl_3$, ppm): 0.91 (t, 3H), 1.65-1.80 (m, 5H), 1.90-2.10 (m, 3H), 2.35-2.50 (m, 2H), 2.55-2.65 (m, 4H), 3.40-3.50 (m, 2H), 4.20 (d, 2H), 4.43 (t, 1H), 6.85 (bs, 1H); $^{13}$C-NMR (400 MHz, $CDCl_3$, ppm): 10.5 ($CH_3$), 18.1 ($CH_2$), 21.1 ($CH_2$), 23.6 (2×$CH_2$), 31.0 ($CH_2$), 43.8 ($CH_2$), 50.1 (2×$CH_2$), 56.7 (CH), 57.2 ($CH_2$), 170.4 (C), 175.8 (C); IR (film, KBr, $cm^{-1}$): 3307, 2966, 1667, 1539, 1288, 1206, 1140.

Example 3

Preparation of N-[(1,1-diethylamino)methyl]-α-ethyl-2-oxo-1-pyrrolidineacetamide 2.3 ml of a 35% w/w solution of formaldehyde in $H_2O$ with 10% methanol were added to a dispersion of 2 g of etiracetam in 4 ml of ethanol at 17° C. 2.4 ml of diethylamine were added immediately after that in 15 minutes without exceeding 25° C., after which the reaction was maintained standing and at room temperature for 4 days. Then the solvent was evaporated under reduced pressure and, after adding 9.6 ml of heptane, the solvent was evaporated again, an operation that was repeated another time, obtaining 3.03 g of the compound indicated in the example title in oil form, characterised by the following analytical data: $^1$H-NMR (400 MHz, $CDCl_3$, ppm): 0.91 (t, 3H), 1.08 (t, 6H), 1.65-1.75 (m, 1H), 1.90-2.10 (m, 3H), 2.35-2.50 (m, 6H), 3.40-3.50 (m, 2H), 4.24 (dd, 2H), 4.44 (t, 1H), 6.75 (bs, 1H); $^{13}$C-NMR (400 MHz, $CDCl_3$, ppm): 10.4 ($CH_3$), 12.8 (2×$CH_3$), 18.1 ($CH_2$), 21.1 ($CH_2$), 31.0 ($CH_2$), 43.8 ($CH_2$), 45.2 (2×$CH_2$), 55.9 ($CH_2$), 56.7 (CH), 170.6 (C), 175.7 (C); IR (film, KBr, $cm^{-1}$): 3316, 2968, 1667, 1539, 1288, 1200, 993.

Example 4

Preparation of (S)-N-[(1-pyrrolidinyl)methyl]-α-ethyl-2-oxo-1-pyrrolidineacetamide L-(+)-tartrate (1:1)

3.14 g of N-[(1-pyrrolidinyl)methyl]-α-ethyl-2-oxo-1-pyrrolidineacetamide were suspended in 13 ml of methanol. 1.86 g of L-(+)-tartaric acid were added and it was heated at 60° C. 13 ml of heptane were added to the resulting solution, after which it was left to cool to 40° C. It was seeded with a sample of the compound indicated in the example title to start crystallisation. Then it was slowly cooled to 0-5° C. and maintained at this temperature for 4 hours. The crystallised product was separated by filtration and washed twice over the filter with 1 ml of methanol each time, and finally once with 6 ml of hexane. 2.86 g of the compound indicated in the example title was obtained with a diastereoisomeric excess (d.e.): 69% measured by means of HPLC analysis of the free base with a chiral column (Chiralcel OD, hexane/isopropanol, 220 nm).

Example 5

Preparation of (S)-N-[(1,1-diethylamino)methyl]-α-ethyl-2-oxo-1-pyrrolidineacetamide L-(+)-tartrate (1:1) in methanol 3.17 g of L-(+)-tartaric acid were added to a suspension of 5.4 g of N-[(1,1-diethylamino)methyl]-α-ethyl-2-oxo-1-pyrrolidineacetamide in 7.4 ml of methanol, and it was heated under reflux. It was left to cool to room temperature and seeded with a sample of the compound indicated in the example title at said temperature to start crystallisation. Then it was cooled to 0-5° C. and maintained at this temperature for 4 hours. The crystallised product was separated by filtration and washed with 2 ml of methanol. 3.16 g of the compound indicated in the example title were obtained with: d.e.: 79% measured by means of HPLC analysis of the free base with a chiral column (Chiralcel OD, hexane/isopropanol, 220 nm). Product recrystallisation obtained from 6.7 ml of methanol allowed obtaining 1.29 g of the compound indicated in the example title characterised by the following analytical data: d.e.: >99.5% measured by means of HPLC analysis on the free base with a chiral column (Chiralcel OD, hexane/isopropanol, 220 nm); IR (film, KBr, cm$^{-1}$): 3283, 2971, 1670, 1546, 1463, 1351, 1215, 1128, 1075.

Example 6

Preparation of (S)-N-[(1,1-diethylamino)methyl]-α-ethyl-2-oxo-1-pyrrolidineacetamide L-(+)-tartrate (1:1) in a methanol/methyl isobutyl ketone mixture 2.95 g of L-(+)-tartaric acid were added to a suspension of 5.02 g of N-[(1,1-diethylamino)methyl]-α-ethyl-2-oxo-1-pyrrolidineacetamide in 6.4 ml of a methanol/methyl isobutyl ketone (4:1) mixture and this was heated at 60° C. It was left to cool at room temperature and was seeded with a sample of the compound indicated in the example title to start crystallisation. Then it was slowly cooled to 0-5° C. and maintained at this temperature for 4 hours. The crystallised product was separated by filtration and washed twice over the filter with 2 ml of methanol each time, obtaining 3.18 g of the compound indicated in the example title characterised by the following analytical data: d.e.: 81% measured by means of HPLC analysis on the free base with a chiral column (Chiralcel OD, hexane/isopropanol, 220 nm). Product recrystallisation obtained from 6.6 ml of methanol allowed obtaining 1.5 g of the compound indicated in the example title with d.e.: >99.5% determined by means of HPLC analysis of the free base with a chiral column (Chiralcel OD, hexane/isopropanol, 220 nm).

Crystallisation was performed in the following solvent systems also with similar results: ethanol; methanol/heptane; ethanol/methyl isobutyl ketone; ethanol/methyl ethyl ketone and methanol/acetone.

Example 7

Preparation of (S)-N-[(1,1-diethylamino)methyl]-α-ethyl-2-oxo-1-pyrrolidineacetamide 1.21 g of (S)-N-[(1,1-diethylamino)methyl]-α-ethyl-2-oxo-1-pyrrolidineacetamide L-(+)-tartrate (1:1) were dissolved in 6 ml of saturated sodium bicarbonate solution and 10 ml of dichloromethane. The phases were separated and the aqueous phase was extracted with dichloromethane (6×10 ml). The pooled organic phases were dried over anhydrous sodium sulfate and subsequently concentrated to dryness. 0.6 g of the compound indicated in the example title was obtained in colorless oil form, characterised by the following analytical data: enantiomeric excess (e.e.) >99.5% determined by means of HPLC analysis with a chiral column (Chiralcel OD, hexane/isopropanol, 220 nm); $[\alpha]^{23}_D$=−71.5° (c=1.01 in acetone).

Example 8

Preparation of Levetiracetam by Deaminomethylation of an Ammonium Salt with Butylamine 5.0 g of (S)-N-[(1,1-diethylamino)methyl]-α-ethyl-2-oxo-1-pyrrolidineacetamide L-(+)-tartrate (1:1) were suspended in 21 ml of a MeOH/H$_2$O (1:1) mixture. 3.6 ml of butylamine were added and the resulting mixture was maintained under stirring at room temperature for 7 hours. Then it was concentrated to dryness. The resulting crude product (8.6 g) was dissolved in 34 ml of dichloromethane, 8.6 ml of saturated sodium chloride solution and 8.6 ml of water. The phases were separated and the aqueous phase was extracted with dichloromethane (6×26 ml). The pooled organic phases were dried over Na$_2$SO$_4$ and finally concentrated to dryness. 2.68 g of a crude product were obtained which was recrystallised twice from methanol, the first time with 2 ml of methanol and the second time with 1 ml of methanol, obtaining 0.76 g of the compound indicated in the example title, characterised by the following analytical data: chemical purity: >99% area/area and (e.e.) >99.8%, both determined by means of HPLC analysis with a chiral column (Chiralcel OD, hexane/isopropanol, 220 nm); $[\alpha]^{23}_D$=−89.8° (c=1.00 in acetone).

Example 9

Preparation of Levetiracetam by Deaminomethylation of an Ammonium Salt in a 1% Methanol/HCl Mixture 5.0 g of (S)-N-[(1,1-diethylamino)methyl]-α-ethyl-2-oxo-1-pyrrolidineacetamide L-(+)-tartrate (1:1) were suspended in 6.2 ml of methanol and 57 ml of a 1% hydrochloric acid aqueous solution. The resulting mixture was maintained under reflux for 12 hours. Then it was concentrated to dryness. The resulting crude product (9.86 g) was dissolved in 25 ml of dichloromethane and 10 ml of saturated sodium chloride solution. The phases were separated and the aqueous phase was extracted with dichloromethane (6×15 ml). The pooled organic phases were dried over Na$_2$SO$_4$ and finally concentrated to dryness. 1.91 g of a solid were obtained which, after successively recrystallising it from methanol, gave similar results as in the previous example.

Example 10

Preparation of Levetiracetam by Deaminomethylation of a Free Amine 0.1 g of (S)-N-[(1,1-diethylamino)methyl]-α-ethyl-2-oxo-1-pyrrolidineacetamide L-(+)-tartrate (1:1) were suspended in 2.5 ml of a MeOH/H$_2$O (1:4) mixture. Then 116 μL of butylamine were added and the resulting solution was maintained under agitation at room temperature for 6 hours. Then the reaction mixture was concentrated to dryness and subsequently recrystallised from methanol, obtaining similar results as those in Example 8.

Example 11

Racemization of (S)-N-[(1,1-diethylamino)methyl]-α-ethyl-2-oxo-1-pyrrolidineacetamide (S)-(II)

0.2 g of (S)-N-[(1,1-diethylamino)methyl]-α-ethyl-2-oxo-1-pyrrolidineacetamide and 8.5 mg of sodium methoxide were suspended in 2.5 ml of methanol and was maintained at 65° C. for 24 hours. The reaction mixture was taken to pH 1-3 with 0.1 N hydrochloric acid and then to pH 8-9 with sodium bicarbonate. Then the aqueous phase was extracted with dichloromethane (3×3 ml). The pooled organic phases were dried over anhydrous sodium sulfate and finally concentrated to dryness. 68 mg of N-[(1,1-diethylamino)methyl]-α-ethyl-2-oxo-1-pyrrolidineacetamide (I) were obtained with d.e.: 8% determined by means of HPLC with a chiral column (Chiralcel OD, hexane/isopropanol, 220 nm).

The invention claimed is:

1. A process for preparing levetiracetam (S)-(I), comprising subjecting the sufficiently pure enantiomer intermediate of general formula (S)-(II) or an addition salt thereof with an acid, to a deaminomethylation reaction,

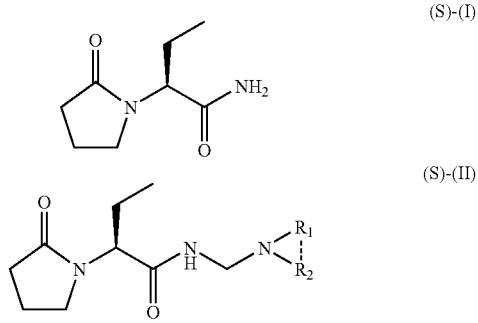

wherein $R_1$ and $R_2$ are the same or different $(C_1-C_6)$-alkyl radicals, or $R_1$ and $R_2$ together with the nitrogen atom to which they are bonded, form a radical selected from the group consisting of 1-pyrrolidinyl, 1-piperidinyl, 1-morpholinyl, 1-piperazinyl and 1-[4-$(C_1-C_4)$ alkylpiperazinyl].

2. A process according to claim 1, wherein $R_1$ and $R_2$ are both ethyl, or $R_1$ and $R_2$ together with the nitrogen atom to which they are bonded form a radical selected from the group consisting of 1-pyrrolidinyl and 1-piperidinyl.

3. A process according to claim 2, wherein $R_1$ and $R_2$ are both ethyl.

4. A process according to claim 1, wherein deaminomethylation is carried out on the sufficiently pure enantiomer intermediate (S)-(II), previously obtained by base treatment of an addition salt of said intermediate with an amine resolving agent acid.

5. A process according to claim 1, wherein deaminomethylation is carried out on an addition salt of compound (S)-(II) with an acid, on a hydrate of said addition salt or on a solvate of said addition salt.

6. A process according to claim 5, wherein deaminomethylation is carried out on an addition salt of compound (S)-(II) with an amine resolving agent acid.

7. A process according to claim 6, wherein the amine resolving agent acid is an enantiomer of an acid selected from the group consisting of tartaric acid, 1-camphor-10-sulfonic acid, malic acid, dibenzoyltartaric acid, mandelic acid, α-methoxyphenylacetic acid, α-methoxy-α-trifluoromethylphenylacetic acid, pyroglutamic acid, ditoluyltartaric acid and 3-bromocamphor-10-sulfonic acid.

8. A process according to claim 7, wherein the amine resolving agent acid is L-(+)-tartaric acid.

9. A process according to claim 1, wherein deaminomethylation is carried out by treatment with an acid.

10. A process according to claim 9, characterised in that said acid is an acid from the group consisting of p-toluenesulfonic acid, methanesulfonic acid, benzenesulfonic acid and hydrochloric acid.

11. A process according to claim 10, wherein the selected acid is hydrochloric acid.

12. A process according to claim 1, wherein deaminomethylation is carried out by treatment with a base.

13. A process according to claim 12, characterised in that said base is a base from the group consisting of ammonia, pyrrolidine, piperidine, 1,2-trans-diaminocyclohexane, diisopropylamine, butylamine, potassium hydroxide and sodium hydroxide.

14. A process according to claim 13, wherein the selected base is butylamine.

15. A process according to claim 1, wherein the addition salt of the sufficiently pure enantiomer intermediate (S)-(II) with an amine resolving agent acid is previously prepared by treating the corresponding racemic intermediate (II)

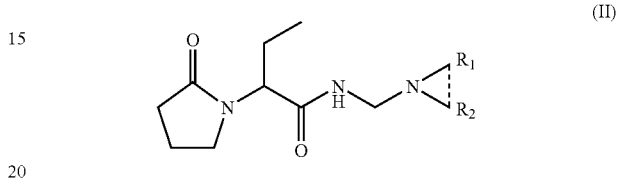

with said acid, followed by one or several selective crystallizations of this diastereoisomeric salt in a solvent system in which said salt is insoluble at a cold temperature; and wherein $R_1$ and $R_2$ have the previously defined meanings.

16. A process according to claim 15, wherein the solvent system is selected from the group consisting of $(C_1-C_5)$ aliphatic monoalcohols, mixtures of $(C_1-C_5)$ aliphatic monoalcohols with $(C_6-C_8)$ aliphatic or aromatic hydrocarbons and mixtures of $(C_1-C_5)$ aliphatic monoalcohols with $(C_3-C_7)$ aliphatic ketones.

17. A process according to claim 16, wherein the solvent system is selected from the group consisting of methanol, ethanol, methanol/heptane mixtures, methanol/methyl isobutyl ketone mixtures, methanol/methyl ethyl ketone mixtures, ethanol/methyl isobutyl ketone mixtures, ethanol/methyl ethyl ketone mixtures and methanol/acetone mixtures.

18. A process according to claim 1, wherein the racemic intermediate (II) is obtained by reaction etiracetam (I)

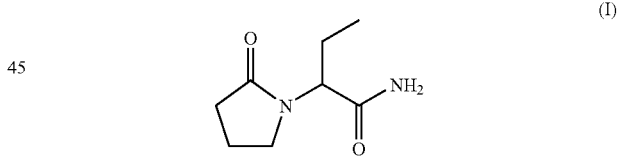

with formaldehyde and an amine of formula $HNR_1R_2$ in an inert solvent; and wherein $R_1$ and $R_2$ have the same meaning as in the previous claims.

19. A process according to claim 1, characterized in that said sufficiently pure enantiomer intermediate of general formula (S)-(II) or an addition salt thereof with an acid, has an enantiomeric excess greater than or equal to 70%.

20. A process according to claim 19, characterised in that said sufficiently pure enantiomer intermediate of general formula (S)-(II) or an addition salt thereof with an acid, has an enantiomeric excess greater than or equal to 80%.

21. A process according to claim 19, characterised in that said sufficiently pure enantiomer intermediate of general formula (S)-(II) or an addition salt thereof with an acid, has an enantiomeric excess greater than or equal to 90%.

22. An intermediate compound of formula (II), its stereoisomers, mixtures thereof solvates, addition salts of any of the foregoing, solvates of said addition salts, and hydrates of said addition salts, wherein $R_1$ and $R_2$ are the same or different $(C_1-C_6)$-alkyl radicals, or $R_1$ and $R_2$ together with the nitrogen atom to which they are bonded form a radical selected from the group consisting of 1-pyrrolidinyl, 1-piperidinyl, 1-morpholinyl, 1-piperazinyl and 1-[4-$(C_1-C_4)$-alkylpiperazinyl]

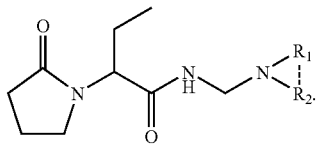

(II)

23. A compound according to claim 22 wherein, $R_1$ and $R_2$ are both ethyl, or $R_1$ and $R_2$ together with the nitrogen atom to which they are bonded form a radical selected from the group consisting of 1-pyrrolidinyl and 1-piperidinyl.

24. A compound according to claim 23, wherein $R_1$ and $R_2$ are both ethyl.

25. A compound according to claim 22, wherein said compound is an addition salt with an amine resolving agent acid.

26. A compound according to claim 25, wherein the amine resolving agent acid is an enantiomer of an acid selected from the group consisting of tartaric acid, 1-camphor-10-sulfonic acid, malic acid, dibenzoyltartaric acid, mandelic acid, α-methoxyphenylacetic acid, α-methoxy-α-trifluoromethylphenylacetic acid, pyroglutamic acid, ditoluyltartaric acid and 3-bromocamphor-10-sulfonic acid.

27. A compound according to claim 26, wherein the amine resolving agent acid is L-(+)-tartaric acid.

* * * * *